United States Patent [19]

Pendleton et al.

[11] 3,970,924

[45] July 20, 1976

[54] APPARATUS FOR DETECTING FAULTS IN MAGNET WIRE INSULATION WITHOUT THERMALLY DAMAGING THE INSULATION AND WHICH DOES NOT RESPOND TO IMPEDANCE INDICATIONS ABOVE A PREDETERMINED THRESHOLD VALUE

[75] Inventors: Wesley William Pendleton; Robert Clifton Thompson, both of Muskegon, Mich.

[73] Assignee: Anaconda Wire & Cable Company, Greenwich, Conn.

[22] Filed: Jan. 16, 1974

[21] Appl. No.: 433,782

Related U.S. Application Data

[60] Division of Ser. No. 170,307, Aug. 9, 1971, Pat. No. 3,823,370, which is a continuation of Ser. No. 876,968, Nov. 14, 1969, abandoned.

[52] U.S. Cl. ............................................ 324/54
[51] Int. Cl.² ...................................... G01R 31/14
[58] Field of Search ..................................... 324/54

[56] References Cited
UNITED STATES PATENTS

| | | | |
|---|---|---|---|
| 2,809,349 | 10/1957 | Miller | 324/54 |
| 2,894,204 | 7/1959 | Gambrill | 324/54 |
| 3,323,701 | 6/1967 | Gurski et al. | 324/54 X |
| 3,413,541 | 11/1968 | Swim et al. | 324/54 |
| 3,491,290 | 1/1970 | Peschel | 324/54 |
| 3,546,581 | 12/1970 | Herrendeen et al. | 324/54 |
| 3,548,302 | 12/1970 | Arnold et al. | 324/54 |

FOREIGN PATENTS OR APPLICATIONS

| | | | |
|---|---|---|---|
| 1,260,728 | 4/1961 | France | 324/54 |

*Primary Examiner*—Gerard R. Strecker
*Attorney, Agent, or Firm*—Pennie & Edmonds

[57] ABSTRACT

Test apparatus is disclosed which provides continuous non-destructive tests for faults in insulation coatings on wire. Means are provided for counting detected faults and actuating an alarm when the fault rate exceeds an undesired limit for any predetermined incremental length of wire. Switch means are provided which automatically adjust measuring sensitivity to correspond with the switch selected D-C test voltage applied to the insulation under test.

3 Claims, 2 Drawing Figures

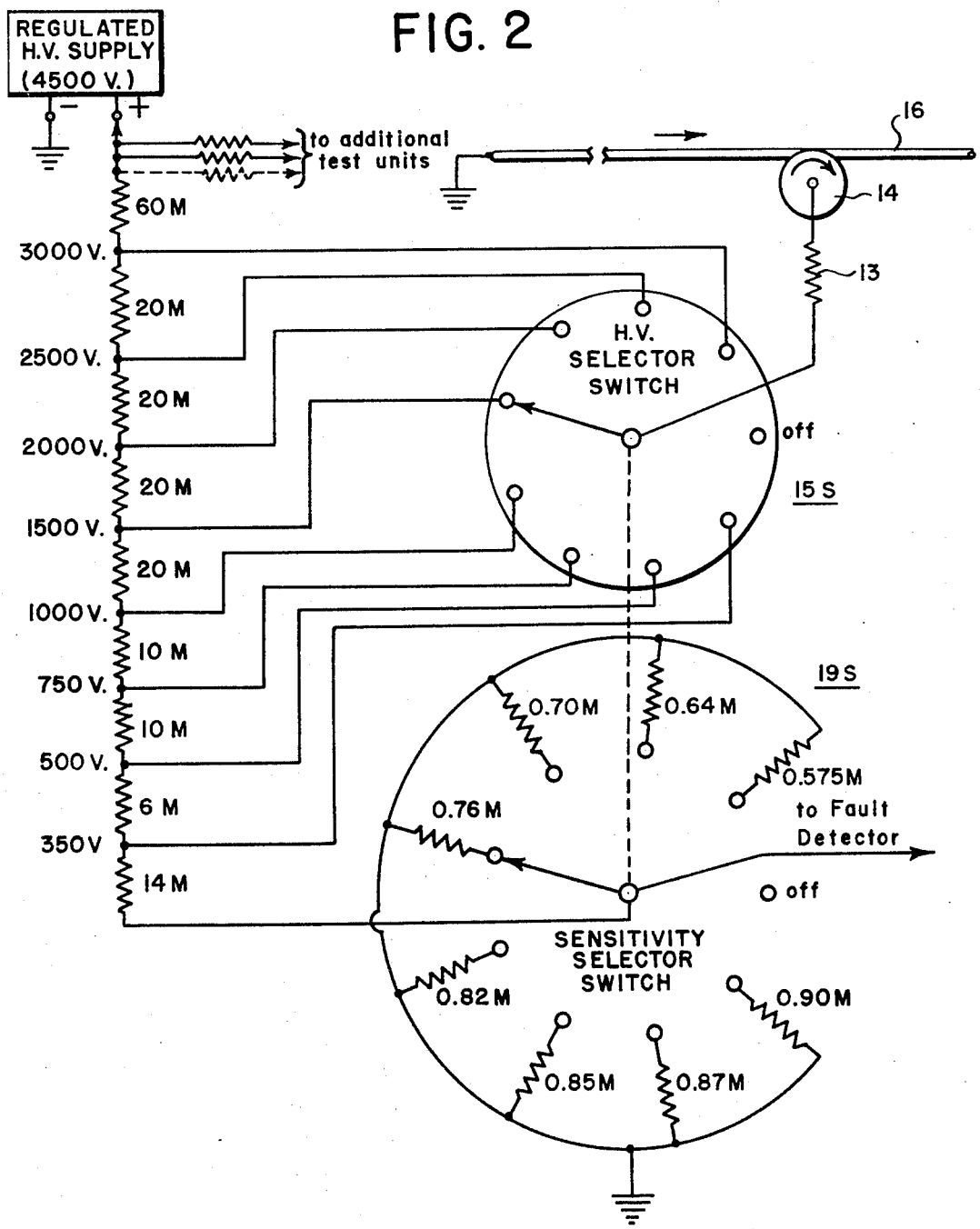

APPARATUS FOR DETECTING FAULTS IN MAGNET WIRE INSULATION WITHOUT THERMALLY DAMAGING THE INSULATION AND WHICH DOES NOT RESPOND TO IMPEDANCE INDICATIONS ABOVE A PREDETERMINED THRESHOLD VALUE

This is a division of application Ser. No. 170,307, filed Aug. 9, 1971, now U.S. Pat. No. 3,823,370 which was a continuation of application Ser. No. 876,968, filed Nov. 14, 1969 now abandoned.

BACKGROUND OF THE INVENTION

The present invention relates to apparatus for electrically testing insulation coatings on wire to detect undesired faults or discontinuities. More particularly, it relates to apparatus for detecting faults in enamel insulation coatings on relatively small magnet wire while the wire is moving at relatively high speeds. Such fault tests are advantageously made immediately after the wire has passed through the enamel curing oven immediately prior to being wound on spools.

Manufacturing standards have been established setting a maximum fault-rate limit of 3, 5 and 10 faults per one hundred feet for triple, heavy and single film insulation coatings, respectively. To have assurance that these industry standards are complied with, it is essential that all manufacturing production of such coated wire be continuously tested. It is desirable of course to make the continuity tests as rapidly as possible; on the other hand, as a practical matter it is difficult to sense and record extremely short duration fault currents generated by small pinhole defects traveling at high speeds past the test instrument. Reliable testing is further complicated by the fact that measuring sensitivity must be increased as a function of insulation thickness and, at the same time, current flow through the insulation voids must be limited to prevent insulation destruction throughout the range of D-C high voltages that are utilized.

One of the time consuming problems encountered with the use of prior art insulation testing devices is that of counting the detected faults (normally recorded on a chart recorder) in order to evaluate production quality based on fault-rate industry standards.

It is a principal object of the present invention to provide a reliable insulation continuity tester which can be quickly adjusted to measure faults in a wide range of coating thickness, and at the same time automatically actuate an alarm indicator when the fault rate exceeds a preselected limit.

DESCRIPTION OF THE INVENTION

The present invention provides a continuous, high-speed, D-C type wire insulation tester with means for adjusting applied test voltage over a wide range of values and at the same time maintaining both a desired level of instrument measuring sensitivity and a limited maximum value of power through the insulation faults to prevent insulation damage.

In a preferred embodiment of the invention, circuit means are provided for converting both short duration pinhole defects and the longer bare-wire defects into uniform pulse widths which can be reliably recorded on inexpensive slow-response recorders. A fault-rate counter is provided with means to actuate an alarm indicator whenever the number of counted faults per incremental length equals or exceeds the desired standard.

DESCRIPTION OF THE DRAWINGS

In the drawings:

FIG. 2 is a circuit diagram showing the test high-voltage and sensitivity selector switches.

Referring to FIG. 1, there is shown high voltage selector switch 10 with high-voltage input terminal 11, and variable output test voltage terminal 12 connected to grooved contact wheel 14 through current limit resistor 13. A predetermined value of D-C high voltage selected by variable voltage selector 15 is applied to test wire 16 (the conductor core of which is grounded as shown) after enamel insulation has been applied. Current flow from wheel 14 through faults in the insulation coating on 16 produce voltage pulses across current sensing resistor 19 which are amplified by current amplifier 20 to a level which is suitable to actuate an adjustable threshold voltage level detector 21 with current pulses produced by the highest resistance pinhole faults desired to be detected (e.g. 80 megohm). Amplifier 20 preferably comprises a plurality of cascaded emitter followers which provide desired high input impedance and a stable current gain characteristic.

Figure 1:
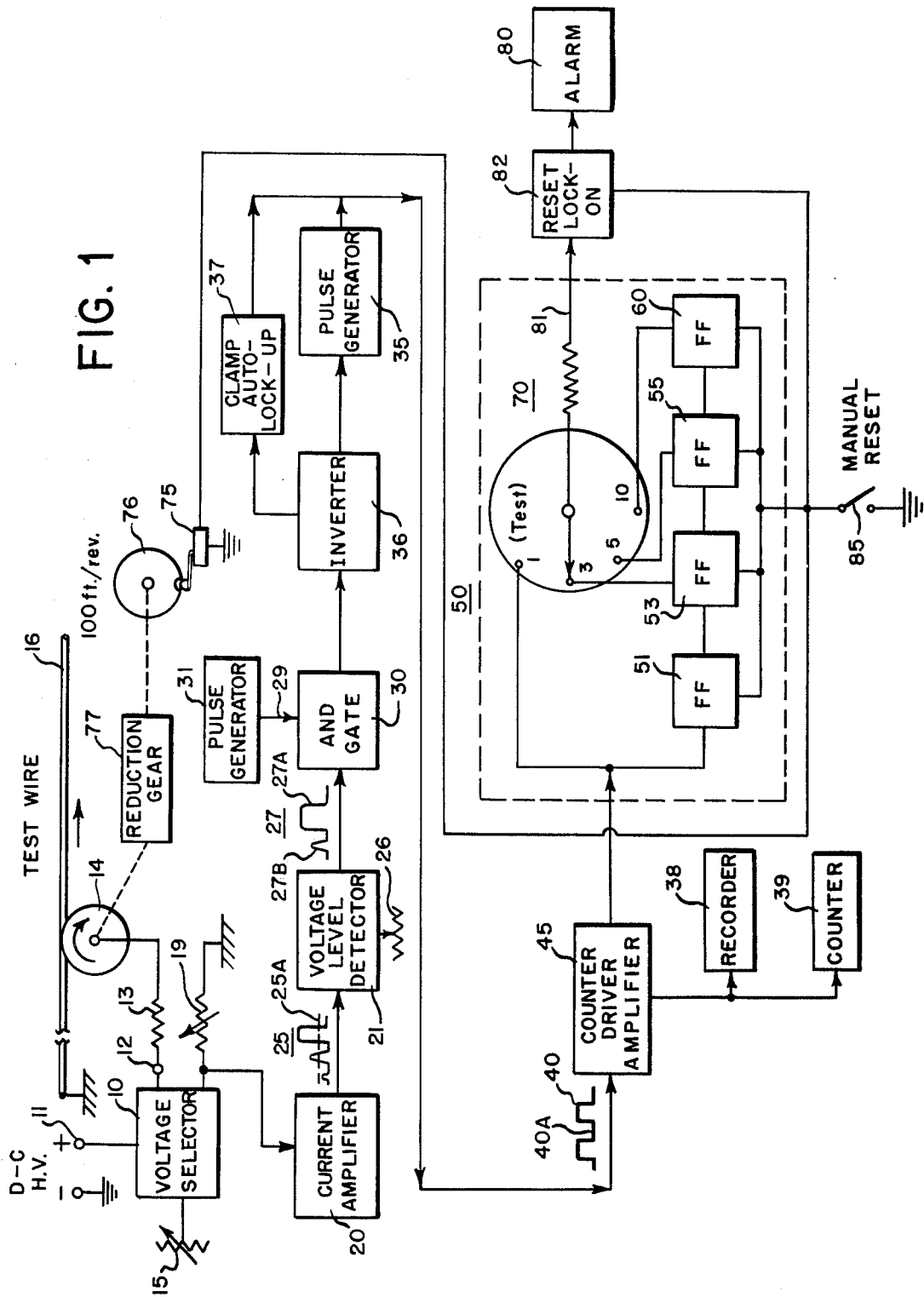
FIG. 1 is a block diagram showing a preferred embodiment of the invention.

Voltage level detector 21 may comprise a differential amplifier one input of which is supplied with varying amplitude fault current pulses 25 and the other input of which is connected to an adjustable threshold level control 26. Level control 26 is set at a desired value to eliminate passage of all fault current pulses below a predetermined amplitude 25A. Current pulses 27 produced by faults exceeding predetermined level 25A are supplied to one input 28 of AND-gate 30 and pulses from pulse generator 31 are supplied to the other input 29. Pulses from 31 serve to close gate 30 at, for example, a one cycle per second rate and thereby provide a continuous fault count of one per second for the longer duration bare-wire faults exemplified by pulse 27A. The on-off duty cycle of the 1 Hz pulses is preferably large (i.e., 20:1) so that gate 30 is maintained in the open position to pass short duration pinhole fault pulses 27B 95% of the time. Output pulses from 30 are supplied to a one-shot pulse generator 35 and clamp auto-lock-up 37 via polarity inverter 36. All fault pulses, those generated by small pinholes as well as the one cycle per second pulses generated by bare-wire defects, are translated by generator 35 to constant width fault-count pulses 40 having sufficient time duration (e.g. 25 msec.) to operate inexpensive solenoid actuated recorder 38 and counter 39 having slow response times. Clamp 37 is advantageously employed to maintain a rest or retention time 40A of approximately 25 msec. between pulses to permit recovery of the electromechanical counter 39. Clamp 37 thereby prevents any pinhole fault signals from being supplied to the counter 39 via driver amplifier 45 until an adequate recovery time has elapsed after each fault count signal.

In accordance with a principal feature of the invention, fault signals from 45 are also supplied to a digital count-down or fault-rate counter 50 comprising four serially connected flip-flops 51, 53, 55 and 60 operatively connected to provide fault-rate alarm control signals of 3, 5 or 10 per 100 feet of wire to the correspondingly indicated terminals of selector switch 70. Countdown 50 is automatically reset to zero fault count by the closing of reset switch 75 once every revolution of cam wheel 76 driven at the rate of one revolution per 100 feet of wire by 14 through reduction gear 77.

Switch 70 may be set to the desired NEMA (National Electrical Manufacturer's Association) limit of 3, 5 or 10 faults per 100 feet as required for testing of triple, heavy or single build insulation and the operator's alarm indicator 80 is actuated by the fault alarm signal supplied by lead 81 to reset lock-on circuit 82 which holds the alarm (visual and/or audible) in the actuated or "on" position until the operator closes manual reset switch 85.

In actual operation, it is desirable to have a relatively wide range of D-C test voltages (e.g., 350V. to 3000V.) available on a switch selected basis in order to facilitate testing of varying insulation film thicknesses (e.g., 0.0002 to 0.0042 inches). At the same time, fault resistance sensitivity changes over a range of from about 10 megohms for thin film coatings to 90 megohms for thick insulation coatings. In accordance with one aspect of the present invention, ganged switch means 15S and 19S are provided as shown in FIG. 2 which simultaneously and automatically modify fault sensitivity to a level appropriate for the test voltage selected by 15S for a given insulation thickness so that the fault current level is maintained substantially constant (e.g. 3 megohms/100 volts applied).

Insulation testers proposed in the prior art have utilized a separate high-voltage power supply to energize each test unit which adds considerably to the overall cost of a multi-unit testing installation. In accordance with one aspect of the present invention, a single regulated high-voltage supply is utilized to simultaneously energize a plurality of operating insulation testers as indicated in FIG. 2. To assure non-destructive testing, current is limited by resistor 13 so that the maximum power supplied to a fault does not exceed 0.15 watts (i.e., product of open circuit test voltage and short circuit current). It has been found that this level is sufficiently high to provide a reliable fault current signal free of cross-talk between plural test instruments operated from a single regulated supply, and at the same time low enough to avoid damage to the wire insulation. Typical parameters are as follows:

| Range of Film Build Inches | AWG Range Single | AWG Range Heavy | AWG Range Triple | D.C. Voltage | Sens. Meg. |
|---|---|---|---|---|---|
| .0002–.0005 | 40–34 | — | — | 350 | 10.5 |
| .0006–.0007 | 33–30 | 40–38 | — | 500 | 15.0 |
| .0008–.0011 | 29–21 | 37–33 | 40–38 | 750 | 22.5 |
| .0012–.0016 | 20–14 | 32–27 | 37–33 | 1000 | 30.0 |
| .0017–.0029 | — | 26–16 | 32–19 | 1500 | 45.0 |
| .0030–.0033 | — | 15–8 | 18–10 | 2000 | 60.0 |
| .0034–.0037 | — | 7–4 | 9–6 | 2500 | 75.0 |
| .0038–.0042 | — | — | 5–2 | 3000 | 90.0 |

It will be appreciated that various changes may be made in the above-described preferred embodiment of the invention. For example, various types of counters may be employed as fault rate counters such as the well known ring, step analog, electromechanical and the like. Similarly, an adjustable timer controlled switch may be utilized in place of the illustrated gear and cam actuated microswitch 80 to periodically reset the fault-rate counter 50.

We claim:
1. Apparatus for continuously testing continuity of the insulation coating on a moving insulated wire conductor, said apparatus comprising:
   a. contact means for applying one of a plurality of D-C high voltage test potentials between the exterior surface of the insulation coating and the interior conductor;
   b. first switching means for selecting any one of the test potentials to be applied;
   c. a current limiting impedance connected in circuit with the contact means for limiting the current through a fault to a value such that the product of the D-C high voltage and the fault current does not exceed about 150 milliwatts;
   d. current sensing impedance means connected in circuit with the contact means, the current sensing impedance means including a plurality of different values of impedance each of which corresponds to one of the test potentials in a predetermined chosen relationship;
   e. second switching means ganged to the first switching means for connecting in the circuit one of the values of impedance as determined by the test potential selected, the value of impedance connected in the circuit being chosen predeterminedly in accordance with the test potential such that the apparatus responds to the highest resistance pinhole fault desired to be detected for the particular thickness of insulation coating under test, each of which resistance pin-hole faults are different for different thicknesses of insulation coating;
   f. threshold amplifying means for amplifying pulses of current flowing through said current sensing impedance means and passing only pulses above a predetermined threshold level; and,
   g. fault-rate counter means for counting the number of fault current pulses for each successive predetermined incremental length of insulated wire.

2. Apparatus in accordance with claim 1 wherein the test apparatus is energized from a common regulated high-voltage supply provided to simultaneously energize a plurality of insulatin testing units.

3. Apparatus as defined in claim 1 wherein the value of the current limiting impedance is selected for each value of applied test voltage such that the fault wattage does not exceed 150 milliwatts and the current sensing impedance means corresponding to each selected value of test potential is chosen so that the maximum impedance fault capable of detection at that test potential is as follows:

| D-C Test Voltage | Sensitivity (Maximum Fault Impedance Capable of Procviding a Fault Indication in Megohms) |
|---|---|
| 350 | 10.5 |
| 500 | 15.0 |
| 750 | 22.5 |
| 1000 | 30.0 |
| 1500 | 45.0 |
| 2000 | 60.0 |
| 2500 | 75.0 |
| 3000 | 90.0. |

* * * * *